(12) United States Patent
Bavington et al.

(10) Patent No.: US 10,294,308 B2
(45) Date of Patent: May 21, 2019

(54) METHOD FOR ISOLATION OF POLYSACCHARIDES

(71) Applicant: ALBERT BARTLETT & SONS (AIRDRIE) LIMITED, Lanarkshire (GB)

(72) Inventors: Charles Daniel Bavington, Oban Highland (GB); Claire Moss, Oban Highland (GB)

(73) Assignee: Albert Bartlett & Sons (Airdrie) Limited, Airdrie (GB)

( * ) Notice: Subject to any disclaimer, the term of this patent is extended or adjusted under 35 U.S.C. 154(b) by 82 days.

(21) Appl. No.: 15/551,531

(22) PCT Filed: Feb. 17, 2016

(86) PCT No.: PCT/GB2016/050400
§ 371 (c)(1),
(2) Date: Aug. 16, 2017

(87) PCT Pub. No.: WO2016/132130
PCT Pub. Date: Aug. 25, 2016

(65) Prior Publication Data
US 2018/0037672 A1 Feb. 8, 2018

(30) Foreign Application Priority Data

Feb. 17, 2015 (GB) .................... 1502668.5

(51) Int. Cl.
| | | |
|---|---|---|
| C08B 37/06 | (2006.01) |
| C08B 37/00 | (2006.01) |
| A61K 31/732 | (2006.01) |
| C12P 19/14 | (2006.01) |
| A61K 31/715 | (2006.01) |

(52) U.S. Cl.
CPC ........ *C08B 37/0003* (2013.01); *A61K 31/715* (2013.01); *A61K 31/732* (2013.01); *C08B 37/006* (2013.01); *C12P 19/14* (2013.01)

(58) Field of Classification Search
None
See application file for complete search history.

(56) References Cited

U.S. PATENT DOCUMENTS 8,962,824 B2 * 2/2015 Zomer ................ A61K 31/715
536/123

FOREIGN PATENT DOCUMENTS

| WO | WO 2003/099309 | 12/2003 |
| WO | WO 2013/059942 | 5/2013 |

OTHER PUBLICATIONS

Obro et al., "Rhamnogalacturonan I in Solanum tuberosum tubers contains complex arabinogalactan structures" Phytochemistry vol. 65 pp. 1429-1438 (Year: 2004).*
Written Opinion and International Search Report Corresponding to International Application No. PCT/GB2015/050400; dated Apr. 22, 2016, 11 pages.
Inge Byg et al, "Large-scale extraction of rhamnogalacturonan I from industrial potato waste", *Food Chemistry*, vol. 131, No. 4, (Sep. 26, 2011) pp. 1207-1216, Abract only.
Meyer A. S. et al., "Enzymatic solubilization of a pectinaceous dietary fiber fraction from potato pulp: Optimization of the fiber extraction process", *Biochemical Engineering Journal*, vol. 43, No. 1, (Jan. 15, 2009), pp. 106-112.

* cited by examiner

*Primary Examiner* — Eric Olson
(74) *Attorney, Agent, or Firm* — Myers Bigel, P.A.

(57) ABSTRACT

A process for the isolation of modified polysaccharide product from potato, in particular a polysaccharide product that can be used as an immunomodulatory is described. More particularly, the extraction and modification of a rhamnogalacturonan I(RG-1) fragment product from a potato using a defined process, and the use of this product to provide immunomodulatory activity to a subject.

15 Claims, 3 Drawing Sheets

METHOD FOR ISOLATION OF POLYSACCHARIDES

FIELD OF THE INVENTION

The present invention relates to a process for the isolation of modified polysaccharide product from potato, in particular a polysaccharide product that can be used as an immunomodulator. More particularly, the present application relates to the extraction and modification of a rhamnogalacturonan I (RG-1) fragment product from a potato using a defined process, and the use of this product to provide immunomodulatory activity to a subject.

BACKGROUND OF THE INVENTION

Pectin is a complex mixture of colloidal polysaccharides found in the primary cell walls of both monocotyledons (monocots) and dicotyledons (dicots) in the plant kingdom. The main polysaccharide structures are homogalacturonan (HGA, commercial food use pectin), rhamnogalacturonan-I (RG-1), and substituted galacturonans. HGA is a linear chain of 1,4-linked α-D-galactopyranosyluronic acid (GalpA) residues in which some of the carboxyl groups are methyl esterified. Rhamnogalacturonan has been called the "hairy region" of pectin. Rhamnogalacturonan-I (RG-1) is a family of pectic polysaccharides that contain a backbone of the repeating disaccharide [→4)-α-D-GalpA-(1→2)-α-I-Rhap-(1→]. 20-80% of the rhamnosyl (Rhap) residues are, depending on the plant source and method of isolation, substituted at C-4 with neutral and acidic oligosaccharide side chains. The predominant side chains contain linear and branched α-I-arabinofuranosyl (Araf), and/or β-D-galactopyranosyl (Galp) residues although their relative proportions and chain lengths may differ depending on the plant source. Some of the side chains may be terminated with α-L-Fucp, β-D-GlcpA, and 4-O-methyl β-D-GlcpA residues. The backbone GalpA is not typically substituted with oligosaccharides. The backbone GalpA residues are O-acetylated in rhamnogalacturonans from many plants. Rhamnogalacturonan-II (RG-II) is not structurally related to RG-1 since its backbone is composed of 1,4-linked-D-GalpA. RG-II has nonasaccharide and octasaccharide side chains attached to C-2 of some of the backbone GalA residues and two structurally different disaccharides are attached to C-3 of the backbone.

Rhamnogalacturonan-I (RG-1) has been previously isolated from many plants and vegetables including potato. Isolated Rhamnogalacturonan-I is typically a polysaccharide with a molecular weight in the 100,000 Da-1000,000 Da size range. When pure, RG-1 is typically soluble in water with low intrinsic viscosity. RG-1 has been discussed to have mitogenic, immunostimulation and antitumor activity.

As the structure, size and composition of RG-1 determines its bioactivity, small changes in structure may confer large changes in activity. Improved selective extraction and purification technologies are required if products are to be available on a large enough scale for health applications. Whilst previous examples of pectin and RG-1 extraction methods have been disclosed for sources such as bell pepper, carrot and apple (US2014/0056946, WO2012/148277), and for sweet potato (CN101627825), they described an alcohol or sodium hydrogen phosphate-based precipitation and purification process. An example of the process of fragmentation of a pectin molecule using free radical depolymerisation, has been disclosed (WO2013/101314), generating a specific mixed HGA-RG-1 product.

Examples of immunomodulatory, mitogenic and antitumour activity of RG-1 containing polysaccharides and oligosaccharides have been disclosed for molecules derived from bell pepper, carrot and apple (US2014/0056946, WO2012/148277) from ginseng (US2012/0278945), from the tea plant Camellia sinensis (US2013/0064858; WO2011/069781) and from citrus and other plant sources (US2011294755; WO2013/101314).

SUMMARY OF THE INVENTION

The inventors have determined that potato and potato waste products (such as whole potatoes, potato fibre after starch removal, potato peel and potato peel after heat treatment, where these are by-product of potato processing such as starch manufacture or production of processed potato products such as chips, crisps and mashed potato) offer a suitable source of rhamnogalacturonan-I (RG-1) due to its high yield.

Whilst RG-1 has previously been extracted from potato using a variety of methods, the present inventors have developed a method of enzymatic extraction, without the use of solvents, which can be scaled up for industrial production. The process generates a non-degraded RG-1 molecule, different in structure from the HGA-RG-1 product which has been disclosed in WO2013/101314. The inventors have also determined that specific fragments of RG-1 can be derived from non-degraded RG-1 by enzymatic digestion or chemical depolymerisation, and these fragments can have applications in immunomodulation, as prebiotics, as nutraceuticals and as cosmetic ingredients.

According to a first aspect of the present invention there is provided a process for the preparation of a fragment of RG-1, wherein the process comprises the steps:

providing RG-1 obtained from the enzymatic extraction of potato preparing a fragment of said RG-1, the fragment having an average molecular weight in the range 5 kDa to 30 kDa, by selective depolymerisation of said RG-1 to provide the fragment wherein the fragment has a monosaccharide composition comprising Arabinose 7-13%,
Rhamnose 5-10%,
Xylose 0-1%,
Galacturonic acid 20-40% and
Galactose 35-60%.

High molecular weight RG-1 polysaccharide can be depolymerised into smaller fragments using techniques such as enzymatic digestion or acid hydrolysis. In embodiments the preparation of a fragment of RG-1 may be by mild acid hydrolysis, cold alkaline conditions or by digestion using non-specific multicomponent enzyme preparations. In embodiments, specific fragmentation can be by selective enzymic digestion of RG-1 using enzymes, which can be selected from rhamnogalacturonan hydrolyases, rhamnogalacturonan lyase, endoarabinase, arabinofuranosidase, endogalactanase, beta-galactosidases, polygalacturonase or combinations thereof. More specifically the process may be by free radical depolymerisation of the RG-1 polysaccharide using photochemical or Fenton chemistry or other free radical methods to cleave glycosidic linkages.

Specifically RG-1 polysaccharide can be depolymerised by introduction of hydrogen peroxide into a RG-1 polysaccharide solution, to generate free radicals, which attack glycosidic bonds. In embodiments, solid RG-1 polysaccharide sample may be added to water at approximately 2 mg/ml and warmed to 60° C. in a water bath. Copper salt solution can then be added to give a 0.01M concentration and the pH was set at pH 7.5 using a pH controller connected to a pump containing sodium hydroxide. The reaction proceeds by pumping hydrogen peroxide into the vessel at a constant flow rate, pH maintained at pH 7 by adding sodium hydroxide. In embodiments, once the reaction has run for the desired period the pH can be lowered using 20% acetic acid and copper chelated using chelex 100. Products can be purified from the reaction by exchange of any remaining copper ions with sodium ions using anion exchange chromatography followed by desalting/separating by size exclusion chromatography using bench columns.

Without wishing to be bound by theory it is considered the RG-1 fragments result from removal or truncation of side chains of RG-1.

In embodiments the fragments of RG-1 can cause no negative effects on the viability of BHK cells after an 18 hour incubation period, using ATP as an indicator of cell activity, wherein a preparation including the fragments shows 95-105% of control values.

In embodiments the fragments obtainable by the process can inhibit neutrophil elastase activity by at least 30-80% when measured in an assay for elastase activity based on release of elastase from human neutrophils stimulated with TNFalpha and fMLP.

The RG-1 fragments of the invention may be differentiated from RG-1 on the basis of lower molecular weight, a monosaccharide profile as set out in the table A below and inhibition of neutrophil elastase:

TABLE A

Where RG-1 is product generated from potato without the fragmentation method described, RG-1-Example A is a highly enzymically purified sample from an expert academic laboratory., Byg 2012 is the RG-1 prepared according to the method described in the paper Byg, Inge; Diaz, Jerome; Ogendal, Lars Holm; Harholt, Jesper; Jorgensen, Bodil; Rolin, Claus; Svava, Rikke; Ulvskov, Peter (2012) Food Chemistry 131, 1207-1216, Byg 2012 + viscozyme is the RG1 fragment prepared according to the method described in that paper, RG1-fragment is the material prepared by the method described here

| Preparation | RG-1 Example B of FIG. 3 | RG-1 Example A of FIG. 3 | Byg 2012 | Byg 2012 + viscozyme RG-1 fragment | RG-1 fragment (present invention) |
|---|---|---|---|---|---|
| MW | >1000 kDa | >215 kDA | 36-210 kDa | 25-40 kDa | <30 kDa |
| Monosaccharide composition % | | | | | |
| Arabinose | 10-15 | 11.7 | 10.74 | 13.8 | 7-13 |
| Rhamnose | 3-6 | 3.9 | 4.51 | 26.7 | 5-10 |
| Galacturonic acid | 6-12 | 6.2 | 10.27 | 41.6 | 20-40 |
| Galactose | 68-78 | 77.5 | 73.35 | 13.6 | 35-60 |
| Mannose | 0-3 | n.d. | NA | NA | 0-5 |
| Fucose | n.d. | n.d. | 0.69 | 1 | n.d. |
| Xylose | 0-1 | n.d. | 0.45 | 3.2 | 0-1 |
| Glucose | 0-1.5 | 0.7 | n.d. | n.d. | 0-5 |
| Ratio GalA: Gal | 0.09-0.15 | 0.08 | 0.14 | 3.12 | 0.57-0.66 |
| Ratio GalA: Rha | 2 | 1.58 | 2.29 | 1.6 | 4 |
| Elastase inhibition % | 0-30% | 0% | NA | NA | 30-80% |

In embodiments potato can be potato and potato waste products (such as whole potatoes, potato fibre after starch removal, potato peel and potato peel after heat treatment, where these are by-product of potato processing for example such as starch manufacture or production of processed potato products such as chips, crisps and mashed potato). Suitably, RG-1 may be obtained from the enzymatic extraction of potato peel.

In embodiments the fragments obtainable by the process can have a molecular weight greater than 5 kDa, greater than 10 kDa, greater than 15 kDa and have a molecular weight less than 30 kDa, more particularly less than 20 kDa, less than 15 kDa.

In embodiments the RG-1 fragment of the invention can be provided by the process at a yield of about 0.5% of the starting potato material.

In embodiments the fragments of RG-1 can comprise 1-3% protein as indicated by a BCA protein assay.

In embodiments the fragments of RG-1 show no presence of sulphur containing molecules as indicated by a sulphate assay based on the method of Terho T & Hartiala K (Method for the determination of sulphate content of glycosaminoglycans. Analytical Biochemistry (1971) 41 (2): 471-476].

Whilst fragments of RG-1 have been reported to have anti-cancer, immunostimulatory and anti-inflammatory properties, the present inventors consider the chain length, and the composition of side chains of the fragments provided by the present process confers differences in activity. It is considered the galactose or arabinose content, i.e. too high or low galactose or arabinose content, or specific ratios of galactose to arabinose can confer different activities including immunostimulatory, anti-cancer, or anti-adhesive effects of fragments not within the scope of the present invention. In particular reduction of arabinose side chains has been reported to enhance binding of RG-1 fragments to galectin 3, which can confer anti-cancer and immunomodulatory activity. Anti-inflammatory properties though a mechanism other than galectin 3 binding are less commonly reported. In the current invention the fragments described having a monosaccharide composition and molecular weight as shown inhibit the release and activity of human neutrophil elastase resulting in an anti-inflammatory effect. Such an effect based on depolymerisation of a purified RG-1 preparation, in particular free-radical depolymerisation, has not been previously disclosed.

According to a second aspect of the present invention there is provide at least one fragment of RG-1 wherein the fragment has molecular weight of less than 30 kDa, a monosaccharide profile according to the table B and which is capable of inhibiting neutrophil elastase.

TABLE B

| Monosaccharide composition | % |
|---|---|
| Arabinose | 7-13 |
| Rhamnose | 5-10 |
| Galacturonic acid | 20-40 |
| Galactose | 35-60 |
| Mannose | 0-5 |
| Fucose | n.d. |
| Xylose | 0-1 |
| Glucose | 0-5 |
| Ratio GalA: Gal | 0.57-0.66 |
| Ratio GalA: Rha | 4 |

In embodiments the fragment can inhibit neutrophil elastase activity by at least 30-80% when measured in an assay for elastase activity based on release of elastase from human neutrophils stimulated with TNFalpha and fMLP.

In embodiments the fragment can have a molecular weight of between 10 kDa to 15 kDa.

According to a third aspect of the present invention there is provided a fragment product according to the process of the first aspect of the invention or a fragment as provided by the second aspect of the invention for use as a medicament.

Suitably the medicament may be for use in treating inflammatory disease. Suitably, the medicament may be for use in the treatment of arthritis, respiratory inflammation, inflammatory bowel disease, or psoriasis.

According to a fourth aspect of the present invention, there is provided a fragment product obtained from the process according to the first aspect of the invention or a fragment as provided by the second aspect of the invention for use as a neutraceutical.

In embodiments the nutraceutical can be used as an alternative to inulin or fructo-oligosaccharide. In embodiments, the nutraceutical is for use as a prebiotic functional food ingredient, or supplement.

The present invention also provides an edible product or pharmaceutical composition comprising a preparation obtained from the process according to the first aspect of the invention or a fragment according to the second aspect of the invention. Preferably the edible product or pharmaceutical composition is suitable for treatment of inflammatory conditions of the intestine. The polysaccharide(s) that is enriched in the preparation according to the invention may be present in the edible product or pharmaceutical composition in its native form, as a constituent of a vegetable material. The edible product according to the present invention may take any physical form. In particular, it may be a food product, a beverage, a dietary food product, or a clinical food product. It may also be a dietary supplement, in the form of a beverage, a tablet, a capsule, or any other suitable form for a dietary supplement. Preferred edible products for incorporation of the fragment obtained from the process according to the first aspect of the invention or the fragment according to the second aspect of the invention are in the form of a liquid, such as a soup or a beverage, a spread, a dressing, a dessert or a bread. If the preferred edible product is a soup, this may be a liquid soup, or a dried soup to which hot water can be added by the consumer. The edible product may be in liquid or spreadable form, it may be a spoonable solid or soft-solid product, or it may be a food supplement. Preferably the edible product is a liquid product.

The concentration of the fragments obtained from the process according to the first aspect of the invention or according to the second aspect of the invention in a food product should be such that modulation of the inflammatory response occurs after consumption of the food product at a regular amount. A regular amount is the amount that an average consumer consumes of such a food product at a specific consumption moment.

In a fifth aspect the present invention provides a fragment product obtained from the process according to the first aspect of the invention or a fragment of the second aspect of the invention for use as cosmeceutical.

In embodiments the cosmeceutical can be used to treat inflammatory skin conditions, for example dermatitis.

In embodiments the preparation can be provided with a pharmaceutically or cosmetically acceptable vehicle for topical applications. Suitably, the vehicle can be selected from a homogeneous phase formulation, an oil in water or water in oil emulsion, cream, liquid solvent, gel or mousse. In embodiments the preparation of the invention can be provided on a wipe, in a spray or fluid.

Suitably a topical composition comprising a fragment obtained from a process of the first aspect or a fragment of the second aspect of the invention may optionally comprise cosmetic adjuncts, pharmaceutical adjuncts or supplements, antimicrobials, antifungals, colourants, lubricants, moisturisers, pH buffering agents, skin permeation enhancers, stabilisers, surfactants, thickeners, viscosity modifiers or vitamins.

Suitably, there is provided the use of a fragment obtained or obtainable from a process of the first aspect of the invention or a fragment of the second aspect of the invention as a cosmeceutical or neutraceutical.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

As used herein, the articles "a" and "an" refer to one or to more than one (for example to at least one) of the grammatical object of the article.

"About" shall generally mean an acceptable degree of error for the quantity measured given the nature or precision of the measurements.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

DESCRIPTION OF FIGURES

Embodiments of the present invention will now be described with reference to the accompanying figures by way of example only in which.

DETAILED DESCRIPTION

Figure 1:
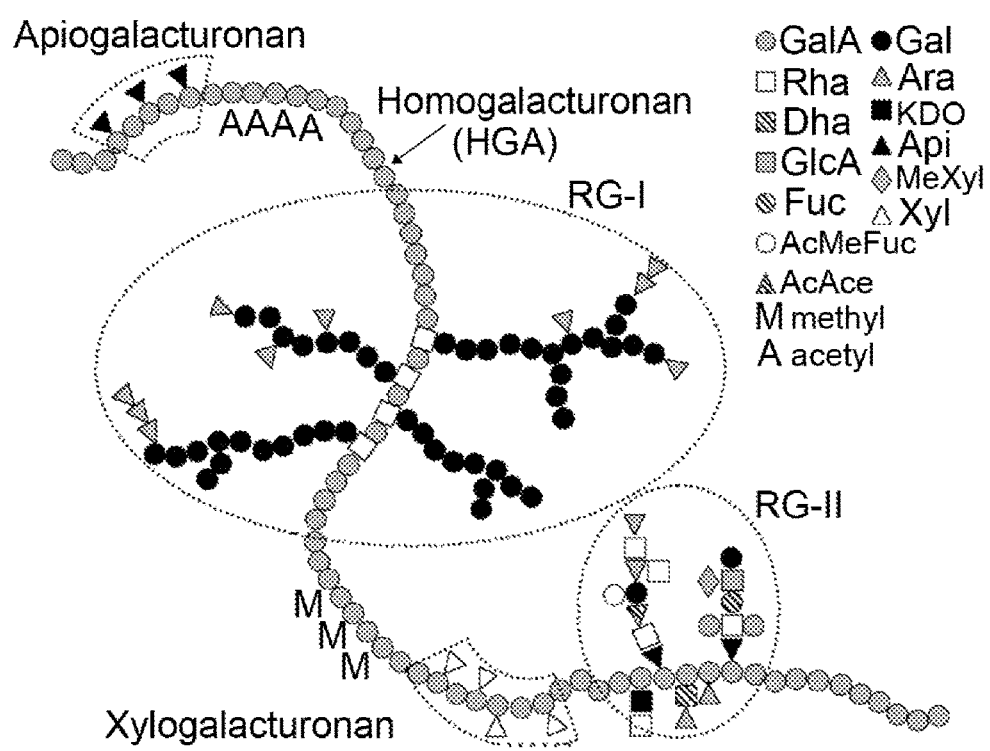
FIG. 1 provides a schematic representation of the primary structure of Pectins as described by Perez (Perez, S., M. A. Rodriguez-Carvajal, and T. Doco, A complex plant cell wall polysaccharide:rhamnogalacturonanII. A structure in quest of a function. Biochimie, 2003. 85(1-2): p. 109W121.)
Figure 2:
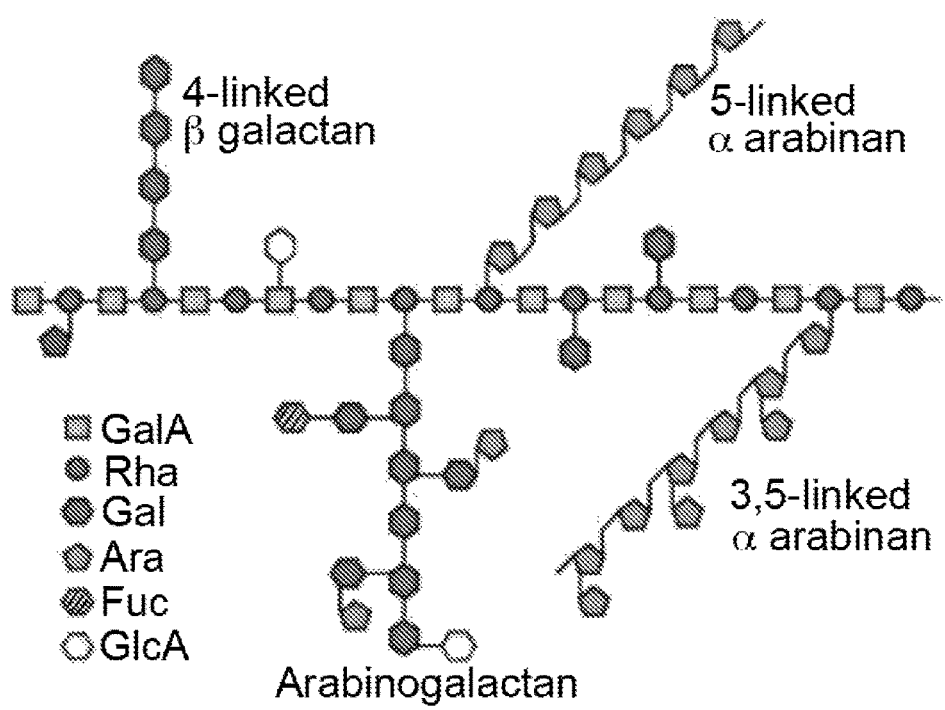
FIG. 2 is a schematic representation of rhamnogalacturonan.

Unless defined otherwise, all technical and scientific terms used herein have the same meaning as commonly understood by one of ordinary skill in the art. All percentages, unless otherwise stated, refer to the percentage by weight. In case a range is given in the context of the present invention, the indicated range includes the mentioned endpoints.

Potato or potato material: in the context of the present invention refers to material from potato origin, in particular potato pulp.

Exemplary Method for Production of RG-1 from Vegetable Material

RG-1 can be extracted from potato material using a variety of maceration methods, followed by chemical or biological extract and digestion processes. More specifically, it can be extracted by blending, heating and enzymatic digestion.

An example method is provided of obtaining RG-1 from the enzymatic extraction of potato. As will be appreciated, other enzymatic extraction processes may be utilised. An appropriate amount of potato material was provided. If the starting material is potato pulp, if appropriate, it is defrosted. If the starting material is whole potatoes they are chopped up into small blocks.

Potato or potato pulp was blended or macerated to create a pulp. The potatoes were heated above 60 C for 15 minutes, until gelatinisation was achieved.

Suitably the potato pulp formed by gelatinisation was cooled to 55 degrees C. prior to treatment to begin enzymatic digestion. The pH was adjusted to pH 5 and 2 ml SAN Extra L, 2 ml AMG 300L and 15 ml Cellitec CTEC2 (Novozymes) were added. The pH was checked to determine it was still pH 5 after addition of the enzymes.

Suitably the potato pulp was transferred to a 2 liter bottle, mixed by hand-shaking and placed in a pre-heated 55 degrees C. incubator. The pulp was hand shaken around every 15 minutes and then left in the incubator overnight at 55 degrees C.

The potato pulp was removed from the incubator and the pH adjusted to pH 8 with 10 mM NaOH. 5 ml of protease (Alcalase-Novozymes) was added and the pH checked again to ensure it was pH 8.

The potato pulp was incubated for a further 6 hours at 60 degrees C., with mixing around every 15 minutes. The digested potato pulp was cooled and spun down at 11000 rpm for 30 minutes.

The resulting supernate was vacuum-filtered through a Whatman number 3 filter and stored frozen. The undigested material was discarded. The supernatant was processed using tangential flow filtration (TFF) on a Pall Centramate system with a 5 kDa molecular weight cutoff membrane. This allowed concentration of the product and diafiltration with water allowed removal of salts, digested protein and other components less than 5 kDa in size. The product was then dried on a Buchi Spray dryer and stored at room temperature.

EXAMPLES

Example 1—Extraction of RG-1

The potato material was added to an appropriate volume of water: 1:10 sample to water ratio for potato pulp (e.g. 100 g potato pulp+1 L RO H2O) or 1:1.5 sample to water ratio for potatoes (e.g. 500 g potato+750 mL RO H2O). The defrosted pulp or potatoes were placed in a saucepan and brought to the boil for 10 minutes to gelatinse the starch.

Amylase and cellulase digestion: The gelatinised material was cooled to 55° C. and the pH adjust to pH 5 with 1N or 0.1N HCl if required. 0.2% of amylase (2 mL AMG 300L and 2 mL SAN ExtraL) to potato pulp preparation (1 L) or 0.27% of each amylase (2 mL AMG 300L and 2 mL SAN ExtraL) to potato preparation (750 mL) was added. 0.5% Cellic CTec2 to potato pulp preparation (5 mL to 1000 mL preparation) or 0.67% Cellic CTec2 to potato preparation (5 mL to 750 mL preparation) was added and the material thoroughly mixed.

The pH was adjusted to pH 5 as necessary and the material transferred to 2 L bottle. The bottle was placed in a pre-heated incubator at 55° C.; and the material mixed by hand-swirling every 15 minutes then left to digest overnight.

Protease digestion: The amylase and cellulase treated material was removed from the oven and the pH adjusted to pH 8 if necessary. 0.5% alcalase was added to the potato pulp preparation (5 mL in 1000 mL preparation) or 0.67% alcalase to potato preparation (5 mL in 750 mL preparation), and the preparation thoroughly mixed. The pH was adjusted to pH 8 if necessary, and the mixture transferred to a 2 L bottle. The mixture was then incubated in a 60° C. preheated oven for approximately 6 hours. The mixture was removed from the oven, cooled to room temperature in room temperature water and then centrifuged at 8500 rpm for 20 minutes. The centrifuged supernate was then filtered through Whatman no. 3 filter paper and the pelleted material discarded.

This supernatant was then subjected to cross flow filtration using a Pall Centramate with a 0.1 m$^2$ 5 kDa molecular weight cut off (MWCO) T-series membrane. Other MWCO's can be used, as long as below MW of polysaccharide. Retentate was re-circulated until concentrated to ×10 original volume. This was then rediluted to original volume and repeated, to ensure salt and media components were removed in the permeate. Conductivity was monitored during the process. The retenate sample was collected and spray dried using a Buchi Mini Spray Dryer B-290 to provide dry polysaccharide powder.

Example 2—Depolymerisation and Oligosaccharide Purification

High molecular weight target RG-1 polysaccharide was depolymerised into smaller fragments using techniques such as enzymatic digestion or acid hydrolysis. Specifically depolymerisation was achieved by introduction of hydrogen peroxide into a polysaccharide solution, to generate free radicals, which attack glycosidic bonds (Rota C et al. 2005 Free radical generation during chemical depolymerization of heparin. Anal Biochem. 344(2): 193-203. and Petit A C et al. 2006 Free-radical depolymerization with metallic catalysts of an exopolysaccharide produced by a bacterium isolated from a deep-sea hydrothermal vent polychaete annelid. Carbohydrate Polymers 64: 597-602.). Solid polysaccharide sample was added to water at approximately 2 mg/ml, dissolved and warmed to 60° C. in a water bath with stirring. Copper salt solution was added to give a 0.01M concentration. Using a pH controller connected to a pump containing sodium hydroxide, the sample was set to pH 7.5. At this point the reaction is started by pumping hydrogen peroxide into the vessel at a constant flow rate, e.g. 0.5 ml/min, with the pH controller set to maintain the pH at 7 by turning the sodium hydroxide pump on when required. Once the reaction had been run for the desired period the pumps were stopped and pH was lowered using 20% acetic acid (5 microL/ml of reaction), chelex 100 (Sigma) was added at 60 mg/ml of reaction and the reaction is mixed on a rotating stirrer until clear. The whole reaction was removed from the chelex and stored at −20° C. Products were purified from the reaction by exchange of any remaining copper ions with sodium ions using Q-sepharose (GE) anion exchange followed by desalting/separating by size exclusion chromatography by Superdex 30 (GE) using bench columns and Buchi Sepacore system with detectors for A214, A280 and conductivity. The Q-sepharose column was equilibrated in 50 mM Tris-HCl pH7.5, 50 mM sodium chloride mobile phase, followed by loading of the depolymerisation reaction, and washing for a further 20-30 mins with mobile phase all at 10 ml/min. Then the bound polysaccharide was eluted with 5M sodium chloride solution and collected. The eluate was added in 5 ml batches to a size exclusion bench column Superdex30 at 1 ml/min with water as mobile phase. Separation was carried out over 120 mins, with 3 ml fractions collected using a Pharmacia fraction collector. Fractions of different polysaccharide molecular weight ranges were identified, pooled, and freeze-dried. Specifically two size ranges were normally collected representing 2-10 kDa and 10-30 kDa derivatives but other sizes may be collected.

Example 3—Determination of Approximate Molecular Weight

RG-1 fragment molecular weight was estimated by size exclusion chromatography using a Waters Alliance HPLC (2695) with Refractive index (Waters 2410) and Photodiode Array (210-380 nm) detection (Waters 996). A shodex SB806M size exclusion column was equilibrated at 30-37° C. in 0.2 micron filtered 50 mM Tris-HCl pH7, 1 mM EDTA, and 0.9% NaCl mobile phase. Column was calibrated using dextran standards (Fluka: 12, 27, 50, 80, 270, 670 kDa), by injecting 20 microL in mobile phase, running at 0.5 ml/min with 30 minute isocratic separations. The standard curve was generated using the formula Kav=(retention time−V0)/(Vt−V0), and plotting Kav versus molecular weight. Samples were injected at 20 microL of a 0.1 mg/ml solution in mobile phase and run as per standards. Data was manually integrated with Millennium Waters software, with or without blank baseline subtraction. The retention times of the sample were compared to those generated for the standard curve to calculate approximate molecular weight using the formula above.

Example 4—Protein Assay

Various methods can be used to determine the amount of protein in an RG-1 preparation from potato. Specifically protein was quantified using a bicinchoninic acid (BCA), which was based on the reduction of copper ($Cu^{2+}$ to $Cu^+$) by protein in an alkaline solution. The BCA chelated the reduced copper and formed a coloured complex, which was measured by its absorbance at 562 nm. The higher the absorbance, the more protein in the sample. A standard curve was prepared using bovine serum albumin in water to give 8 standards between 0-2000 µg/ml protein. The Lambert-Beer Law was used to accurately determine the protein content of each batch of standards, which were then aliquoted and frozen until use. Samples were prepared at 1 mg/ml in water, and a second set of samples were prepared at 1 mg/ml in water with 0.5 mg/ml BSA (spiked samples), to check for any assay interference by the sample. The BCA working solution was prepared by mixing 50 parts BCA solution with 1 part of 4% cupric sulphate. 25 µl of each blank, standard, sample and spiked sample was pipetted into the well of a 96 well plate (in triplicate). 200 µl of BCA working solution was added to each well, the plate was mixed on a plate shaker for 30 minutes and then incubated at 37° C. for 30 minutes. The plate was then allowed to cool to room temperature for 15 minutes. Colour intensity was measured in an absorbance microplate reader (BioTek Power Wave HT) at 562 nm using Gen5 software. Mean absorbance values (from triplicates) were calculated for each well, and the mean blank absorbance was subtracted from all other test wells. The corrected absorbance of the standards was plotted against the Lambert-Beer corrected protein values to generate a standard curve. The standard curve equation was used to calculate the amount of protein present in the samples and spiked samples, any dilution factors were taken in to account and protein was expressed in mg/ml of sample. Spiked recovery was calculated for each sample (based on the value for the 0.5 mg/ml BSA standard) and the accepted range was 75-125% recovery.

Example 5—Determination of Approximate Sulphate Content

Various methods may be used to determine sulphate content of RG-1 fragment. Specifically sulphate determination was carried out based on a method by Terho T & Hartiala K (Method for the determination of sulphate content of glycosaminoglycans. Analytical Biochemistry (1971) 41 (2): 471-476). 25 µl of 1 mg/ml sample or control (chondroitin Sigma C4384 or heparin Sigma H3393) in water was placed in a reaction vial. 1M HCl was added to give a final concentration of 0.5-1M HCl and the vials heated at 100° C. for 2 hours. The hydrolysed sample was rotary evaporated using a Speed Vac (Jouan RC10/10 with RCT60 refrigerated trap) under vacuum at 60-65° C. until dry (usually 1-2 hours). The dried hydrolysate was dissolved in 250 microL of water (0.1 mg/ml).

Standards were prepared from 1 mM sulphuric acid to give concentrations in the assay of 0.048, 0.096, 0.192, 0.288, 0.384, 0.432, 0.48 µg sulphate. 100 microL of each sample, standard, control or blank (water only) were pipetted into an eppendorf, to which 400 microL of ethanol was added and mixed thoroughly. 125 microL of this mix was added to triplicate wells of a 96 well assay plate, 50 µl BaCl$_2$ buffer (freshly prepared 0.2M Acetic acid, 0.1 mM barium chloride, 1.6 mM sodium hydrogen carbonate all in absolute ethanol) was added to each well, followed by 75 µl sodium rhodizonate solution (freshly prepared 0.05 mg/ml, 1 mg/ml L-ascorbic acid in absolute ethanol). The plate was shaken at medium speed for 30 secs, incubated in the dark for 10 minutes and shaken again. Colour intensity was measured in an absorbance microplate reader (BioTek Power Wave HT) at 520 nm using Gen5 software. Absorbance was calculated by subtracting the mean absorbance for each sample, standard or control from the mean absorbance of the blank. A standard curve was generated by plotting the blanked absorbance against the sulphate concentration for each sulphuric acid standard, and the sulphate content of samples and controls was interpolated. This value is corrected for dilutions and volumes to give % sulphate= ((Mean∆A520×40)/50)×100.

Example 6—Determination of Monosaccharide Composition

Monosaccharide composition can be determined using a number of different methods. Specifically, monosaccharide composition was determined by methanolysis and trimethylsilane (TMS) derivatisation followed by composition analysis using Shimadzu GC-2014 with flame ionisation detection (GC-FID). Reaction vials were heat cleaned in a furnace oven for 6 hours at 450° C. 100 microg of sample (as a 10 mg/ml solution) was transferred to a vial and 5 nmol of scyllo-inositol internal standard was added to each sample. A vial containing 5 nmol of each monosaccharide standard was also set up containing scyllo-inositol (18132 Sigma), arabinose (A3131 Sigma) xylose (X-1500 Sigma), mannose (M6020 Sigma), fucose (F2252 Sigma), rhamnose (R3875 Sigma), galactose (G0750 Sigma), glucose, glucosamine (G4875), galactosamine (G0500), glucuronic acid (G5269), galacturonic (48280 Fluka), sialic acid (all prepared as 100 mM stock solutions). All vials were dried in a speed-vac (Jouan RC10/10 with RCT60 refrigerated trap) under vacuum at 60-65° C. until dry (usually 1-2 hours). 40 microL of neat methanol was added, the samples dried again as above and then resuspended in 100 microL of 0.5M methanolic HCl. The vials were heated at 85° C. in a heat bloc for 4 hours. After cooling 20 microL neat pyridine was added to neutralise the HCl and 20 microL neat acetic anhydride was then added to re-N-acetylate any free primary amines (for 30 minutes at room temperature). The vials were then dried again (speed vac as above), 40 microL of neat methanol was added to wash, the vials were re-dried (10-30 mins speed vac as above). 40 microL of neat TMS reagent was then added and mixed thoroughly to resuspend the sample. The vials were sealed and left for at least 10 minutes before injecting 1 microL onto a Shimadzu GC-2014 with flame ionisation detection (300° C. splitless injection). The column was ZB5-ms, 30 m×0.25 mm i.d.×0.25 µm film thickness. The chromatograms generated were analysed. The area cut off was manually adjusted for each sample until 20-30 peaks were identified. Peak areas and retention times were correlated with the monosaccharide standards.

Each peak was calculated:

ratio=peak area/internal standard peak area;

standard ratio=standard area/internal standard area for each standard;

nmoles=(5 nmoles/standard ratio)×sample ratio;

% of each monosaccharide present in the original sample=nmoles/total nmoles×100.

Example 7—Determination of Effects on BHK Cell Viability

Various different cell-based screening assays can be used to determine the cytotoxicity of the target material. Specifically cytotoxicity is examined by measuring the effects of the RG-1 polysaccharide and RG-1 oligosaccharide derivatives on the metabolic activity of a BHK cell line (hamster kidney fibroblast ECACC 85011433). 90% confluent BHK cells are harvested and plated in a 96-well white microplate at 1×10$^4$ cell/well in 100 microL freshly prepared culture media (Glasgow Minimum Essential Medium (GMEM), 10% Foetal Calf Serum, 5% Tryptose Phosphate Broth, 2 mM L-Glutamine). They are left for 1 hour at 37° C. 5% CO$_2$ to allow >80% adhesion to the well. 11 microL of 1 mg/ml poysaccharide sample in Hanks Balanced Salt Solution (HBSS), HBSS only control, fucoidan (1 mg/ml in HBSS) control, and doxorubicin (10 microg/ml, 1 microg/ml in HBSS) controls are added to triplicate wells and the plate incubated for 16-18 hours at 37° C. 5% CO$_2$. The plate is allowed to come to room temperature for 30 minutes before additions of 100 microL Cell titre glow reagent (Promega). Plate is mixed for 2 minutes on a plate shaker and then incubated for 10 minutes at room temperature. The resulting luminescence for each well is measured on plate reader (BioTek, Synergy 3) using Gen5 software. Mean luminescence for each sample or control is calculated. The HBSS control well is designated as 100% metabolic activity and sample luminescent values are calculated against this % activity=(test well/control well)*100. The fucoidan and doxorubicin controls should be within established values.

Example 8—Effects on Neutrophil Elastase Activity

Different protocols are possible for the measurement of the effect of RG-1 fragments on neutrophil elastase enzyme activity. Specifically elastase activity was measured by incubation of RG-1 fragments with stimulated freshly isolated human neutrophils followed by reaction of released enzyme with a labelled substrate and colourimetric measurement on a plate reader. Freshly isolated human neutrophils were resuspended in HBSS (without Ca and Mg) and cells counted on a haemocytometer. The cells were centrifuged and resuspended in HBSS to give a concentration of 2.5×10$^6$ cells/ml. 22 microL of sample, controls or HBSS were added to a microtube followed by: 25 microL of cytochalasin B (at 40 mg/ml in HBSS to give a final concentration 5 mg/ml); 25 microL of TNF a (at 80 ng/ml in HBSS to give a final concentration of 10 ng/ml, with 25 microL HBSS used in place of TNF a for a non-stimulated control); 150 microL of neutrophil suspension (or for a media only control group add 150 microL of HBSS in place of cells). Contents were gently mixed and the tubes incubated at 37° C. for 30 minutes. After incubation 25 microL of fMLP (at 1 microg/ml in HBSS to give a final concentration of 100 ng/ml) was added, or HBSS to the non-stimulated control group. Tubes were incubated for a further 45 minutes at 37° C. Tubes were centrifuged at 5000 rpm for 5 minutes on a Heraeus Biofuge to pellet the cells and 25 microL of the supernatant is transferred into triplicate wells of a 96 well black microplate. 150 microL of Tris HCl pH 7.5 and 20 microL of neutrophil elastase substrate 1 (0.5 mg/ml in Tris-HCl pH 7.5) were added to each well, except for a blank well which contains no substrate. The plate was transferred to a pre-warmed (37° C.) plate reader (BioTek Powerwave HT) and readings are taken at 405 nm every 5 minutes for 1 hour using Gen5 software. Vmax was calculated over 4 data points between 10 minutes and 1 hour. Mean Vmax was calculated for each sample, control or blank. The control well (stimulated cells with substrate, but no test samples) Vmax was designated as 100% and samples and controls are calculated against this to generate % elastase activity: % activity=(test well Vmax/control well Vmax)*100.

Figure 3:
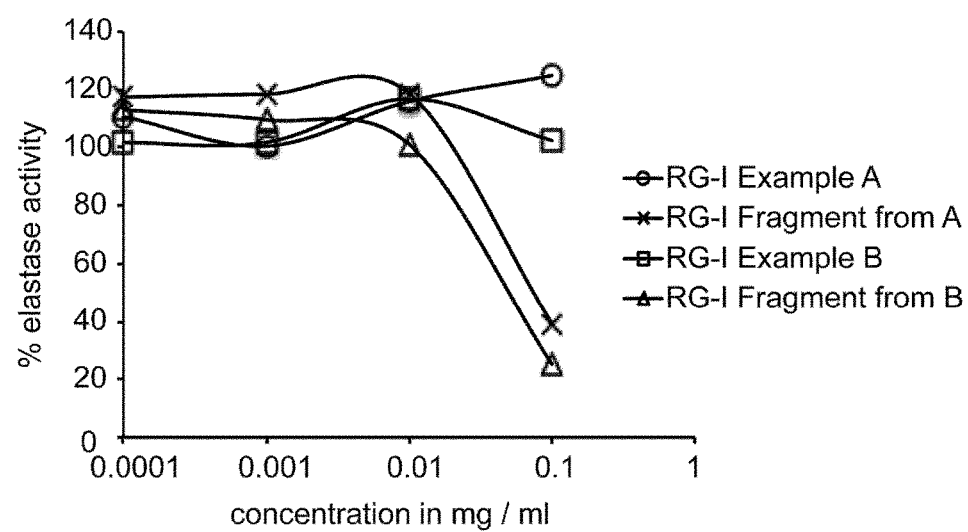
FIG. 3 illustrates the effect of high molecular weight RG-1 polysaccharides and of oligosaccharides derived from RG-1 on the activity of neutrophil elastase. RG-1 Example A is a highly enzymatically purified laboratory potato RG-1 from an expert academic laboratory. RG-1 Fragment from A is a product from free radical polymerisation of Example A, MW=12.2 kDa, RG-1 Example B is a product generated from the enzymatic extraction of potato as described herein and RG-1 fragment B is a product from free radical depolymerisation of Example B, MW=11.6 kDa.

Results for this example are provided by FIG. 3.

Although the invention has been particularly shown and described with reference to particular examples, it will be understood by those skilled in the art that various changes in the form and details may be made therein without departing from the scope of the present invention.

The invention claimed is:

1. A process for the preparation of a fragment of RG-1, wherein the process comprises the steps:
   providing RG-1 obtained from the enzymatic extraction of potato
   preparing a fragment of said RG-1, the fragment having an average molecular weight in the range 5 kDa to 30 kDa, by selective depolymerisation of said RG-1 to provide the fragment wherein the fragment has a monosaccharide composition comprising
   Arabinose 7-13%,
   Rhamnose 5-10%,
   Xylose 0-1%,
   Galacturonic acid 20-40% and
   Galactose 35-60%.

2. A fragment of RG-1 wherein the fragment has molecular weight of less than 30 KDa, which is capable of inhibiting neutrophil elastase and comprises a monosaccharide profile

| Monosaccharide composition | % |
|---|---|
| Arabinose | 7-13 |
| Rhamnose | 5-10 |
| Galacturonic acid | 20-40 |
| Galactose | 35-60 |
| Mannose | 0-5 |
| Fucose | n.d. |
| Xylose | 0-1 |
| Glucose | 0-5 |
| Ratio GalA: Gal | 0.57-0.66 |
| Ratio GalA: Rha | 4. |

3. A fragment obtained from a process comprising
   providing RG-1 obtained from the enzymatic extraction of potato
   preparing a fragment of said RG-1, the fragment having an average molecular weight in the range 5 kDa to 30 kDa, by selective depolymerisation of said RG-1 to provide the fragment wherein the fragment has a monosaccharide composition comprising
   Arabinose 7-13%,
   Rhamnose 5-10%
   Galacturonic acid 20-40% and
   Galactose 35-60%.

4. A method of treatment at least one of inflammatory disease, arthritis, respiratory inflammation, inflammatory bowel disease, and psoriasis in a subject in need thereof, said method comprising administering the fragment according to claim 2 to said subject.

5. A method of treatment of at least one of inflammatory disease, arthritis, respiratory inflammation, inflammatory bowel disease, and psoriasis in a subject in need thereof, said method comprising administering the fragment according to claim 3 to said subject.

6. A neutraceutical composition comprising the fragment according to claim 2.

7. A cosmeceutical composition comprising the fragment according to claim 2.

8. A composition comprising the fragment according to claim 2, wherein said composition is a medicament, a neutraceutical or a cosmeceutical.

9. A method of treating an inflammatory disease comprising administering an RG-1 fragment of claim 2 to a subject in need thereof.

10. The method of claim 9, wherein the inflammatory disease is at least one condition selected from arthritis, respiratory inflammation, inflammatory bowel disease, and psoriasis.

11. A neutraceutical composition comprising the fragment according to claim 3.

12. A cosmeceutical composition comprising the fragment according to claim 3.

13. A composition comprising the fragment according to claim 3, wherein said composition is a medicament, a neutraceutical or a cosmeceutical.

14. A method of treating an inflammatory disease comprising administering the fragment of claim 3 to a subject in need thereof.

15. The method of claim 14, wherein the inflammatory disease is at least one condition selected from arthritis, respiratory inflammation, inflammatory bowel disease, and psoriasis.

* * * * *

UNITED STATES PATENT AND TRADEMARK OFFICE
CERTIFICATE OF CORRECTION

PATENT NO. : 10,294,308 B2
APPLICATION NO. : 15/551531
DATED : May 21, 2019
INVENTOR(S) : Bavington et al.

It is certified that error appears in the above-identified patent and that said Letters Patent is hereby corrected as shown below:

In the Specification

Column 8, Line 35:
Please correct "15 minutes" to read -- ~15 minutes --

Column 11, Line 31:
Please correct "(18132" to read -- (I8132 --

Column 12, Line 48:
Please correct "TNF a" to read -- TNF α --

Column 12, Line 50:
Please correct "TNF a" to read -- TNF α --

In the Claims

Column 14, Lines 7-8, Claim 3:
Please correct
"Rhamnose 5-10%
Galacturonic acid 20-40% and" to read
-- Rhamnose 5-10%
Xylose 0-1%
Galacturonic acid 20-40% and --

Column 14, Line 10, Claim 4:
Please correct "treatment at" to read -- treatment of at --

Signed and Sealed this
Twenty-fourth Day of September, 2019

Andrei Iancu
*Director of the United States Patent and Trademark Office*